United States Patent
Christensen et al.

(10) Patent No.: US 6,645,183 B2
(45) Date of Patent: Nov. 11, 2003

(54) CATHETER WITH ADJUSTABLE FLOW RATE

(75) Inventors: James M. Christensen, Glendora, CA (US); Steven J. Fix, Corona, CA (US); John A. Krug, Orange, CA (US)

(73) Assignee: Advanced Infusion, Inc., Tempe, AZ (US)

(*) Notice: Subject to any disclaimer, the term of this patent is extended or adjusted under 35 U.S.C. 154(b) by 135 days.

(21) Appl. No.: 10/046,098

(22) Filed: Nov. 8, 2001

(65) Prior Publication Data

US 2002/0115966 A1 Aug. 22, 2002

Related U.S. Application Data

(63) Continuation-in-part of application No. 09/400,579, filed on Sep. 22, 1999, now Pat. No. 6,569,128.

(51) Int. Cl.⁷ .................................................. A61M 5/00
(52) U.S. Cl. ...................................... 604/246; 604/244
(58) Field of Search ........................... 604/244, 246, 604/264, 272–274, 534, 535, 538, 158, 164.01, 93.01, 161, 164.06, 164.07, 164.11, 412, 523

(56) References Cited

U.S. PATENT DOCUMENTS

| | | | |
|---|---|---|---|
| 3,094,124 A | | 6/1963 | Birtwell |
| 3,951,147 A | | 4/1976 | Tucker et al. .............. 128/260 |
| 4,386,929 A | | 6/1983 | Peery et al. ................. 604/132 |
| 4,741,733 A | | 5/1988 | Winchell et al. .............. 604/51 |
| 5,989,239 A | * | 11/1999 | Finch et al. ................ 604/502 |
| 6,059,737 A | * | 5/2000 | Crawford .................... 600/576 |
| 6,068,613 A | * | 5/2000 | Kriesel et al. .............. 604/132 |

* cited by examiner

Primary Examiner—Sharon Kennedy
Assistant Examiner—Kevin C. Sirmons
(74) Attorney, Agent, or Firm—Koppel, Jacobs, Patrick & Heybl; Michael J. Ram

(57) ABSTRACT

A micro-bore catheter for use with an infusion pump wherein the micro-bore lumen of the catheter acts as an adjustable flow restricting element. The flow rate through the catheter can be increased proportionally by trimming the length of the catheter. One end of the catheter is attached to a needle for insertion of the catheter into the elastomeric septum of a drug infusion pump.

2 Claims, 3 Drawing Sheets

CATHETER WITH ADJUSTABLE FLOW RATE

This application is a continuation-in-part of Ser. No. 09/400,579 filed Sep. 22, 1999 and now U.S. Pat. No. 6,569,128.

BACKGROUND OF THE INVENTION

1. Field of the Invention

The present invention generally relates to a liquid delivery tube, and more particularly, to a catheter for delivering medication to a patient, the catheter being constructed from micro-bore tubing attached to a needle. The needle is attached to the external surface of the tubing so that it does not restrict the flow of fluid through the tubing. The tubing has a uniform internal diameter along its entire length. When used to deliver, under a fixed pressure, a liquid medication of a known viscosity the flow rate of the liquid can be closely controlled by cutting the microbore tubing to a desired predetermined length

2. Description of the Prior Art

It is well known in the industry that the flow rate of a fluid from an infusion device can be controlled by a flow restricting orifice, tube, or micro-passage of various configurations. There are several common embodiments of this art in commercial use today. U.S. Pat. No. 3,951,147 to Tucher, et al, describes several flow restrictors including a long stainless steel tube which is wound around the infusion pump body, a long spiral groove formed by inserting a threaded wire into a tube, and other similar configurations.

U.S. Pat. No. 4,386,929 to Peery, et al, discusses a short capillary tube contained within the pump housing for regulating the flow rate of medication dispensed. He also mentions other types of flow restrictors such as porous plugs, fiber bundles, and porous films, all of which are contained within the pump housing.

The devices described in Tucher et al and Perry et al all suffer from the disadvantage that in order to change the flow rate, a different pump must be used. This creates an inventory problem for users who wish to utilize a specific flow rate at the time of application of the infusion pump. In addition, these infusion pumps generally do not provide the capability of delivering fluid to more than one catheter at a time since each catheter would require its own flow restrictor to insure a proper flow rate through the catheter.

U.S. Pat. No. 3,094,124 to Birtwell discloses a large bore arterial having a tapered tip with a small diameter opening. The tapered tip is marked in intervals to assist a user in cutting the catheter to a desired outer diameter to match the diameter of a severed arterial into which it is to be inserted for recirculation of blood during an open heart procedure. In the Birtwell devices the flow through his catheter is controlled by the diameter of the outlet opening or a attachable stainless steel cannula inserted in that opening. The internal diameter of the remainder of the catheter is not taken into consideration and flow is not controlled by severing a predetermined length of the catheter. Instead, flow is controlled by varying the size of the end of the tapered portion of the catheter.

U.S. Pat. No. 4,741,733 to Winchell, et al, discloses a flow restrictor placed external to the pump body in the delivery tube system. This system can be used where multiple catheters are required to adequately infuse medication into the body. The flow restrictor disclosed consists of a short restrictor tube, usually a glass micro-bore tube, contained within a plastic housing.

In current practice, the flow restrictor housing can be removed from the infusion device delivery system, branching connectors added, and flow restrictors, each optionally having different flow rates, added to the infusion system. In this way, multiple catheters having different flow rates can be achieved. However, it is still necessary that an inventory of flow restrictors having different flow rates be maintained so the user can select from a variety of flow rates at the time of application of the infusion device.

In order to overcome the need to maintain an inventory of catheters having different flow rates, it would be desirable to have a catheter whose flow rate could be easily adjust at the time of use. Such a catheter would enable only one catheter to be inventoried yet allow the user to adjust the flow through the catheter to any flow rate desired at the time of use.

SUMMARY OF THE INVENTION

Accordingly, the objects of the current invention are to provide a new and improved catheter for dispensing fluids and medications from an infusion device, the improved catheter having a lumen through its length providing flow restriction along the entire length of the catheter tubing such that the flow rate can be adjusted at the time of use. In a preferred embodiment the internal diameter of the tubing (i.e., the lumen diameter) is closely controlled to be a consistently uniform along its full length. Such tubing may be referred to as a calibrated flow, microbore tubing.

In accordance with these and many other objects of the current invention, a catheter tube embodying flow restriction along its entire length can have its flow rate adjusted by trimming the length of the flow restricting catheter tube. The tubing could be trimmed at the time of manufacture or could be trimmed at a later time of use. Length markings to aid in trimming the catheter tubing could be placed on the outside of the catheter with ink, laser ablation, or other suitable method of marking.

The flow restricting catheter tubing can be any flexible micro-bore tubing that can be easily trimmed without distorting the trimmed end. The catheter tubing is attached to the elastomeric septum of the infusion device by a needle which is adhered to one end of the catheter tubing.

As the flow restricting catheter tubing is shortened by trimming, the flow rate will increase in linear proportion to the decrease in initial length of the catheter tubing. If the tubing is cut in half, the flow rate will double.

BRIEF DESCRIPTION OF THE DRAWINGS

The present invention, together with the above and other objects and advantages, can best be understood from the following detailed description of the embodiment of the invention illustrated in the drawings, wherein.

DETAILED DESCRIPTION OF THE PREFERRED EMBODIMENT

Figure 1:
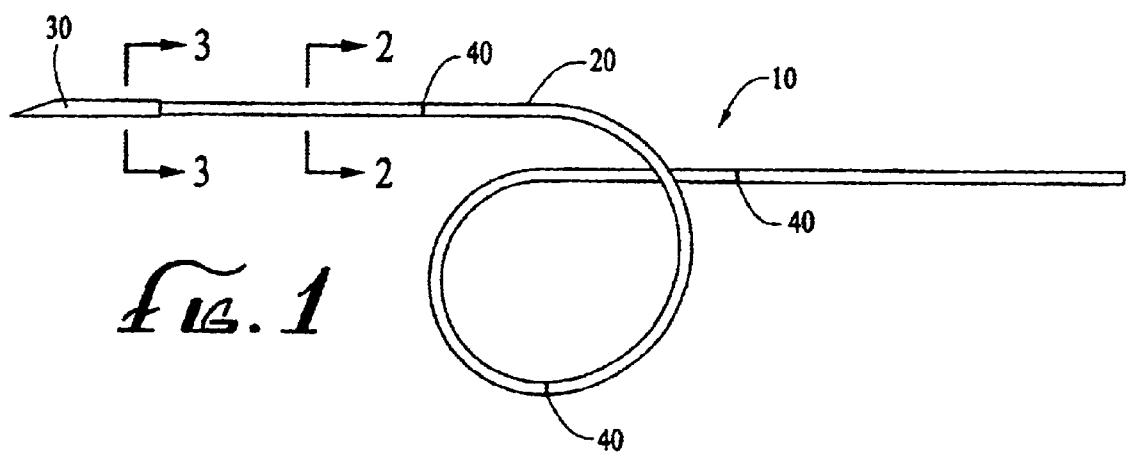
FIG. 1 is a side view of the catheter tubing and needle assembly embodying the present invention.

Referring now more specifically to FIG. 1 an infusion catheter 10 is shown. The infusion catheter 10 is comprised of a length of micro-bore tubing 20 with a needle 30 attached to the outside of the tubing 20 at the tubing's proximal end. A series of markings 40 may be placed along the length of the catheter 10 on the catheter outer surface to aid the user in trimming the catheter in order to alter its flow rate.

Micro-bore tubing 20 can be constructed from various different materials including materials which are currently used in the industry to form catheters. These materials are plastics or elastomers, including polyvinylchloride, polyurethane, polyethylene, polyamide, silicone elastomer, and Teflon. Micro-bore tubing is generally extruded, although other methods of manufacture may be used. No requirements are placed on the materials of the tubing other than it have a consistent inner diameter and can be trimmed without deforming and/or closing its trimmed end.

The needle 30 can be constructed from various materials such as stainless steel, rigid plastics, or ceramics. The needle may be pointed or blunt (cannula) as both styles can be caused to puncture through a soft elastomeric septum used for access purposes for attachment of the catheter. A needle point cover or protector (not shown), used to prevent accidental needle sticks of personnel using the device, as is sometimes required by regulatory bodies may also be applied to the device. Various techniques can be used to attach the needle 30 to the outside of the micro-bore tubing 20, such as adhesives, heat bonding, or a mechanical interference caused by shrinking or expanding one of the materials involved. Typically, an acrylic based adhesive such as cyanoacrylate is used to bond the needle to the tubing.

Markings 40 may be placed along the outside of the tubing 20 to aid in trimming the catheter in order to adjust flow rate. Preferably these makings may be printed onto the outside of the tubing with a suitable ink or etched into the tubing using a laser. The markings may also be placed on the outside of the tubing by some other suitable means such as stamping, melting, chemical etching, or similar processes. Still further, the markings can be applied during extrusion of the tubing by periodically applying a different colored plastic or a molten colorant.

Figure 2:
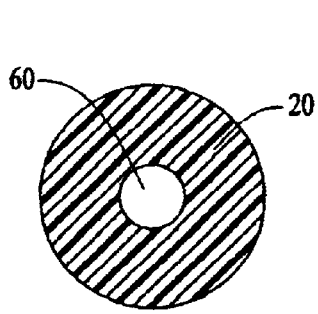
FIG. 2 is a cross-sectional view taken along line 2—2 of FIG. 1 showing the flow restricting catheter tubing
Figure 3:
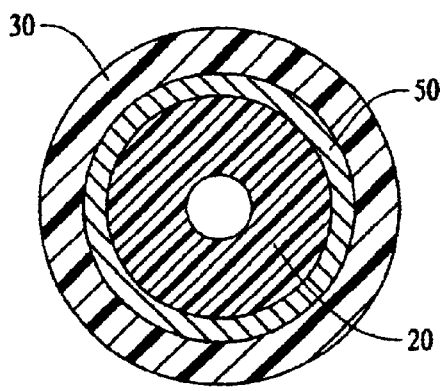
FIG. 3 is a cross-sectional view taken along line 3—3 of FIG. 1 showing the flow restricting catheter tubing and attached needle.

FIGS. 2 and 3 show cross sectional views of the infusion catheter 10 taken at two locations along the length of the catheter. FIG. 2 shows a cross sectional view of the micro-bore tubing 20 taken along line 2—2 of FIG. 1 including a uniform central lumen 60 along the full length of the tubing 20 through which the fluid flows. The diameter of the lumen 60 is selected to achieve the desired flow rate of the medication through the infusion catheter. It is important that this lumen 60 be the same diameter throughout the entire length of the tubing 20 so that the flow rate can be accurately adjusted by trimming the length of the infusion catheter 10.

FIG. 3 is a cross sectional view through the needle 30 and micro-bore tubing 20 taken along line 3—3 of FIG. 1 located near the assembly junction between the tubing 20 and the needle 30. The needle 30 is placed over the proximal end of the micro-bore tubing 20. An adhesive 50 is preferably applied between the two components in order to adhere them together. This adhesive may be any suitable adhesive such as cyanoacrylate, epoxy, a UV or visible light cured adhesive, or similar material. Preferably an acrylic based cyanoacrylate having low viscosity is used which will wick into the space between these two components then quickly set up.

The dimensions of the lumen 60 in the micro-bore tubing 20 can be determined from Poiseuille's Law as expressed in the equation:

$$Q = (Pr^4)/8Ln$$

where Q is the flow rate in cc/sec, P is the pressure drop through the tube in dynes/cm$^2$, r is the internal radius of the tube in cm, L is the length of the tube in cm, and n is the viscosity in poise.

From this equation it can be seen that flow rate is inversely related to the length of the micro-bore tubing 20. For example, if the tubing is cut in half, the flow rate doubles. It can also be seen that the flow rate is related to the fourth power of the radius of the lumen 60. A small change in the radius or diameter of the fluid path 60 can have a major change on the flow rate. For example, for a 48" long catheter operating at 6 psi, if the diameter of the fluid path is increased from 0.0044" diameter to 0.0052" diameter the flow rate will double. From this relationship, suitable micro-bore tubing can be chosen which will provide the desired flow rate for a specific length of infusion catheter attached to an infusion device which delivers medication at a specific pressure.

Figure 4:
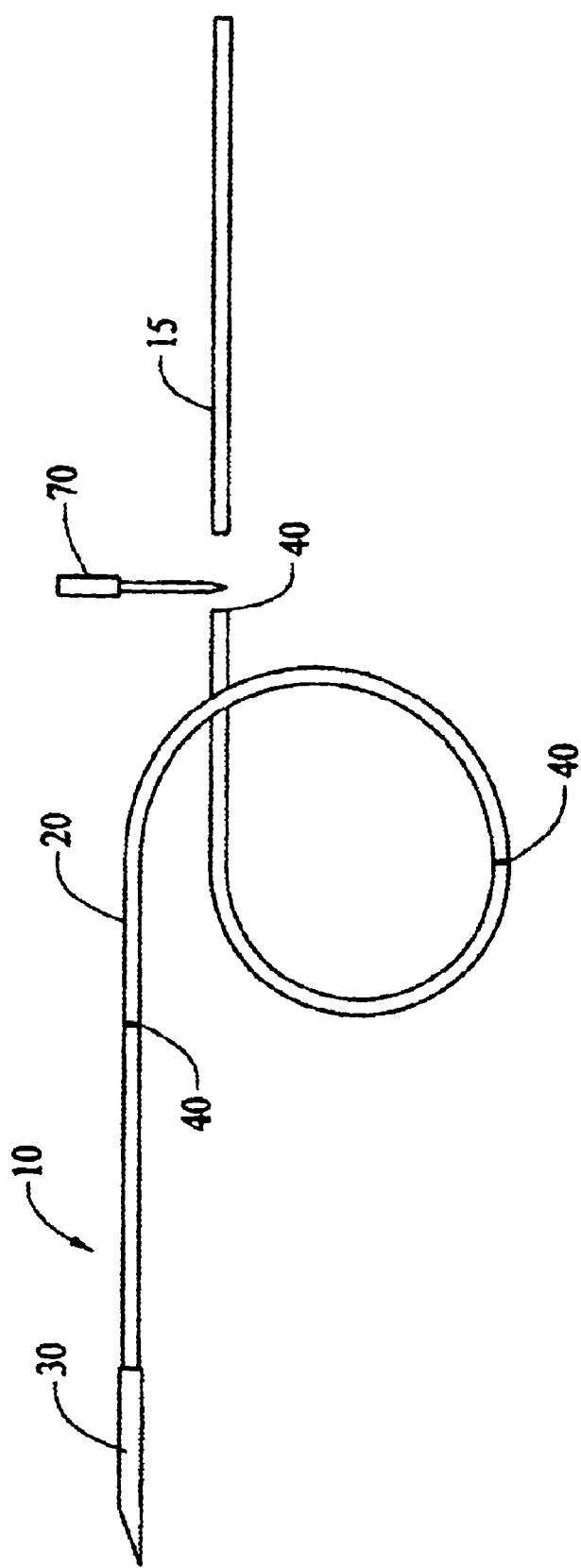
FIG. 4 is a side view showing the flow restricting catheter tubing being trimmed to achieve an increased flow rate.

FIG. 4 shows the infusion catheter 10 as it is trimmed to length. A sharp instrument, such as the knife blade 70 can be used to cut and remove a section 15 from the infusion catheter thereby altering the flow rate through the catheter. The shortened infusion catheter will now have a proportionately higher flow rate based on the ratio of the original length divided by the shortened length. For example, if ¼ of the length of the catheter were cut away leaving a catheter ¾ of the original length, the new flow rate would be 4/3 times the original flow rate since flow rate is inversely proportional to length. From this relationship the spacing of the trim markings can be calculated before they are placed on the catheter. The markings will allow a surgeon to trim the catheter just prior to use so as to achieve the desired flow rate from the catheter at the time of surgery.

In a preferred embodiment, ten infusion catheters were constructed from 90D durometer polyvinyl chloride micro-bore tubing. Micro-bore tubing with two lengths and five different internal diameter were selected. A stainless steel needle was attached to one end of each piece of tubing to form an infusion catheter. Each infusion catheter was connected to a drug infusion device operating at a pressure of 6 psi. The flow rate obtained through each of the infusion catheters is given in the chart below:

| Infusion Catheter Fluid Path Diameter for a given Flow Rate @ 6 psi | | | | | |
|---|---|---|---|---|---|
| Length | 0.5 ml/hr | 1.0 ml/hr | 2.0 ml/hr | 4.0 ml/hr | 5.0 ml/hr |
| 48" long | .0044" | .0052" | .0062" | .0074" | .0078" |
| 24" Long | .0037" | .0044" | .0052" | .0062" | .0066" |

While seven different diameter of micro-bore tubing from 0.0037" to 0.0078" internal diameter were utilized, one skilled in the art will recognize that any tubing having a consistent, uniform internal diameter can be used as long as the internal diameter is sufficiently small to achieve the flow rate there through and to allow the flow rate to be readily varied when the tubing length is adjusted.

Preferred micro-bore tubing lumen diameters range from about 0.001" to about 0.010" when micro-bore tubing from about 24" to about 48" in length is a selected. These dimensions are appropriate when the liquid medication being delivered has a viscosity similar to water and a pump pressure of about 6 psi is used. If the pump pressure is raised or lowered or the liquid delivered has a higher viscosity, the internal diameter of the micro-bore tubing used to form the catheter should be appropriately adjusted.

It is possible that minor variances in the internal diameter of the micro-bore tubing will occur due to manufacturing inaccuracies. These variances can cause a large variation in the flow rate through the infusion catheter since flow rate varies as the fourth power of the lumen diameter. During construction of the infusion catheter, the actual flow rate of the catheter can be measured and the catheter trimmed to obtain a more accurate flow rate. In this way precise flow rate infusion catheters can be manufactured.

Figure 5:
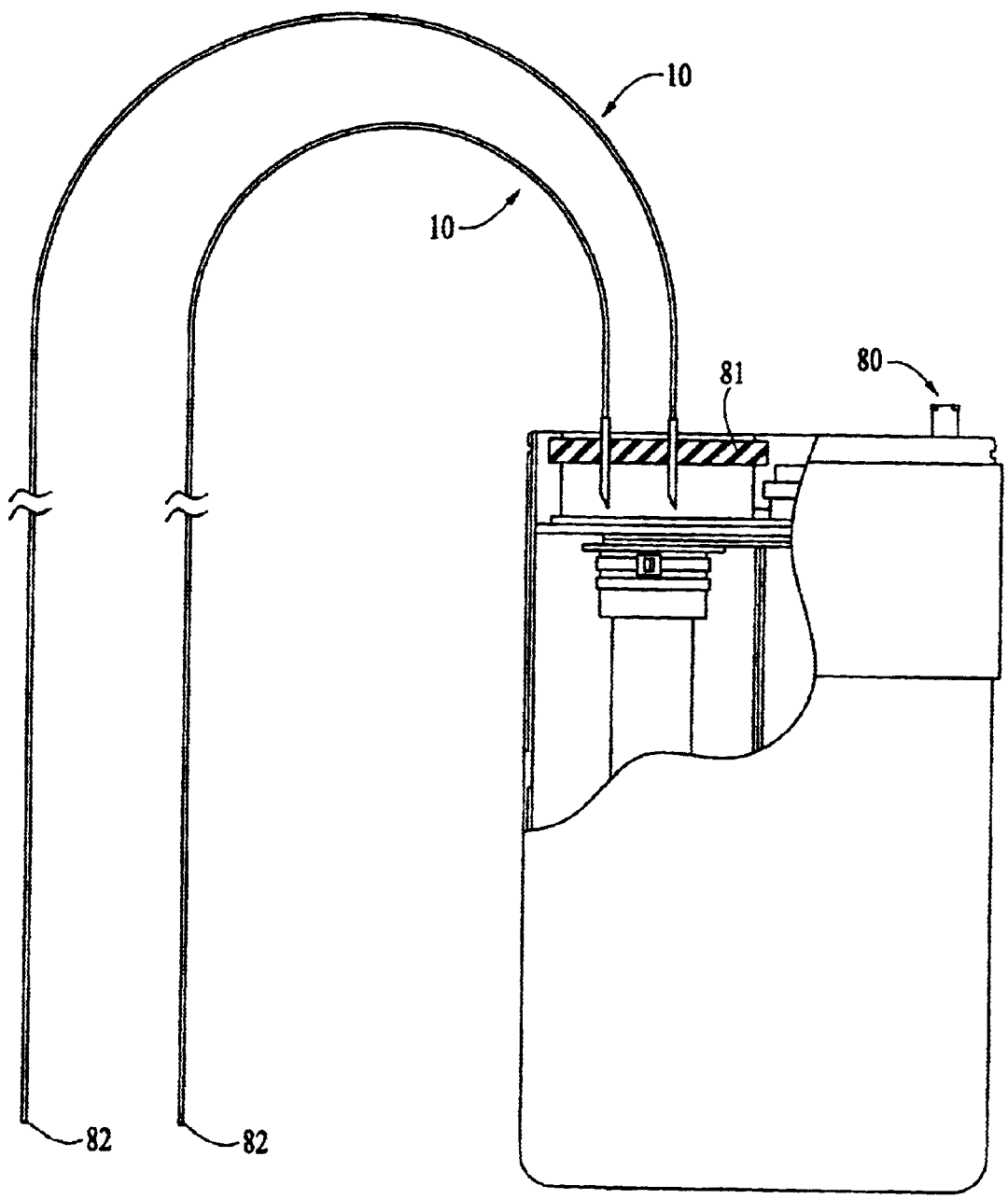
FIG. 5 is a view showing a preferred embodiment of the flow restricting catheter attached to the elastomer septum of a drug infusion device.

FIG. 5 shows two infusion catheters 10 incorporating features of the invention inserted into an elastomeric septum 81 of an infusion pump device 80 designed to supply medication at a constant pressure. Multiple catheters may be inserted into the septum without the need for branching "Y" assemblies and flow restrictor components outside the pump. Such components are typically required for most currently available pumps. The trimmable outflow end 82 of each of these infusion catheters 10 may be placed in a different area of the patient's body using standard catheter insertion techniques to achieve the desired flow rates.

It is evident from the foregoing that there are many additional embodiments of the present invention which, while not expressly described herein, are within the scope of this invention and may suggest themselves to one of ordinary skill in the art. It is therefore intended that the invention be limited solely by the appended claims.

We claim:

1. A catheter for the continuous infusion of a liquid medication from a drug delivery device into a patient comprising:

a micro-bore tubing having a uniform internal diameter of from about 0.001" to about 0.010", the micro-bore tubing having a first and a second end and a length from about 24 inches to about 48 inches, a needle attached to an outside surface of the micro-bore tubing at the first end of the micro-bore tubing, the needle being insertable through a puncturable wall of the drug delivery device, the micro-bore tubing being severable at a selected point between the first end and the second end in order to change the flow rate of the liquid medication passing there through to a predetermined greater flow rate, the internal diameter and the length of the micro-bore tubing, in combination, being chosen such that the micro-bore tubing, once severed provides the predetermined flow rate through the catheter when the drug delivery device is operated at a predetermined delivery pressure.

2. The catheter of claim 1 wherein the internal diameter of the micro-bore tubing is from about 0.0037" to about 0.0078".

* * * * *